United States Patent [19]

Hernestam et al.

[11] 4,344,952
[45] Aug. 17, 1982

[54] METHOD OF TREATING DIARRHOEA WITH GAMMA-PIPERIDINO-BUTYROPHENONES

[75] Inventors: Sven E. H. Hernestam, Malmö; Kjell B. Martinsson, Ballingslöv; Erik G. Christensson, Lund; Nils-Göran E. Olsson, Ödåkra, all of Sweden

[73] Assignee: AB Ferrosan, Malmö, Sweden

[21] Appl. No.: 154,863

[22] Filed: May 30, 1980

[51] Int. Cl.³ .......................................... A61U 31/445
[52] U.S. Cl. ..................................................... 424/267
[58] Field of Search ......................................... 424/267

[56] References Cited

U.S. PATENT DOCUMENTS 4,021,563 5/1977 Hernestram ........................ 424/267

FOREIGN PATENT DOCUMENTS 1142143 2/1969 United Kingdom.

OTHER PUBLICATIONS

Amer. J. of Physiology, vol. 227, No. 6, Dec. 1974, pp. 1436–1443.

Field, Aba Foundation Symposium 42, 1978 pp. 109–127.
Infection & Immunity, Jun. 1979, vol. 24, No. 3, pp. 900–905.
Dissert. Pharm. Pharmacol., 1970 XXII 2B, pp. 105–116.
Acto Veterinaria Scandenavica, Supp. 41, (1973) pp. 77–79.
Nordisk Vetenarimedicin 27(2) 1975, pp. 86–101.

*Primary Examiner*—Stanley J. Friedman
*Attorney, Agent, or Firm*—Abelman, Frayne & Rezac

[57] ABSTRACT

A method of treating diarrhoea and promoting weight gain in mammals by administration of an effective amount of a compound selected from the group consisting of 4-fluoro-γ-(4-alkylpiperidino)-butyrophenone of the formula

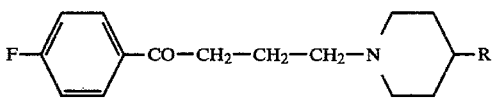

wherein R is lower alkyl having 1 to 6 carbon atoms, or pharmaceutically acceptable acid addition salts thereof.

6 Claims, No Drawings

METHOD OF TREATING DIARRHOEA WITH GAMMA-PIPERIDINO-BUTYROPHENONES

BACKGROUND OF THE INVENTION

This invention relates to a method for treating diarrhoea in mammals caused by strains of bacteria producing enterotoxins, i.e. *E. coli, V. cholerae* and *C. perfringens,* by administering a 4-fluoro-γ-(4-alkylpiperidino)-butyrophenone of the formula

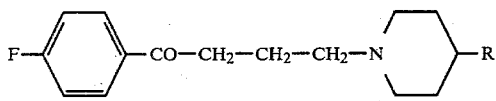

wherein R is lower alkyl having 1 to 6 carbon atoms, or pharmaceutically acceptable acid addition salts thereof.

The compounds have shown pronounced effect on for example travellers diarrhoea in man and diarrhoea associated with *E. coli* in pigs. Diarrhoea often is caused by enterotoxins from different bacterial strains that stimulate the adenylate cyclase/cyclic AMP system in the intestinal mucosa (Field, M. Ciba Foundation Symposium 42, Elsevier 1978, Amsterdam). Mucosal adenylate cyclase is also stimulated by diarrhoegenic hormones like vasoactive intestinal peptides and prostaglandins, thus supporting the concept that there exist cyclic AMP regulated transport mechanisms for electrolytes and fluid across the intestinal mucosa. By such mechanisms a prolonged stimulation of adenylate cyclase induces profuse diarrhoea followed by dehydration and sometimes death.

The mechanism of the adenylate cyclase system in the intestinate membranes is indeed complex and at present not known in detail. Although cyclic-AMP stimulated secretion appears to be electrogenic for anion it is nevertheless $Na^+$-dependent. Removal of $Na^+$ (from the bothing medium) abolishes net $Cl^-$ secretion (Powel et al., Am. J. Physiol. 1974, 227, 1436).

An inhibitor of the adenylate cyclase system, chlorpromazine (The Merck Index 9th Ed., 2175) has been tested for its effect on diarrhoea caused by *E. coli* in piglets (Lönnroth et al., Infect. Immun. 1979, 24, 900–905). In addition to a repressing effect of chlorpromazine on diarrhoea certain disadvantages exist such as reduction in blood pressure, pronounced sedation at a dosage required for clinical effect, slow elimination and the risk of inducing contact allergy. Due to the sedation piglets treated with chlorpromazine often will be trampled and crushed by the mothersow. Lönnroth (4th International Symposium on Phenothiazines and Related Drugs, Zurich, Sept. 9–13, 1979) investigated butyrophenones as to their effect on intestinal secretion and reported that they have no or very little effect on intestinal secretion in contrast to sedative phenothiazines. However, through comprehensive research work the inventors have found that melperone (4-fluoro-γ-(4-methyl-piperidino)-butyrophenone) of the formula

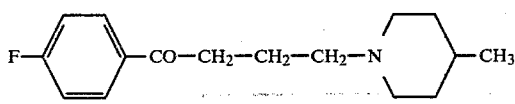

(compound and process for the preparation thereof known from British Pat. No. 1,142,143), a butyrophenone characterized by few motoric, central and autonomic side effects (Ventulani et al., Pharm. Pharmacol. 1970, 22, 105), has an inhibiting effect on the intestinal adenylate cyclase system evaluated by the gut fluid secretion test (test system described by Lönnroth et al., Infect. Immun. 1979, 24, 900–905).

Hitherto a great number of different antibiotics have been used to treat diarrhoea associated with strains of *E. coli*. In vitro tests and clinical experience have shown a pronounced bacterial resistance against the antibiotics used. Therefore, the principle of treating these diseases through enzyme inhibition, without the risk of resistance, is superior. Furthermore, the effect of an enzyme inhibitor (such as melperone according to the invention) compared to antibiotics may be more rapid since the effect is directed to the target organ and not indirectly via the killing of the causative microorganisms. This suggestion is supported by the results in experiment II below and partly also by the trials with the previously suggested compound chlorpromazine (Lönnroth et al., Infect. Imm. 1979, 24, 900–905).

The litter morbidity of diarrhoea in piglets, 0–5 weeks old, is about 15–20% in affected herds and the mortality about 70–100% (1–2 pigs/litter) (Bäckström, Acta Vet. Scand. suppl. 41, 1973; Svendsen et al., Nord. Vet. Med. 1975, 27, 85–101).

SUMMARY OF THE INVENTION

Thus, our invention relates to a method of treating diarrhoea in mammals caused by strains of bacteria producing enterotoxins, i.e. *E. coli, V. cholerae* and *C. perfringens,* by administration of an effective amount, such as 0.1 to 20 mg per kg body weight of a compound selected from the group consisting of 4-fluoro-γ-(4-alkylpiperidino)-butyrophenone of the formula

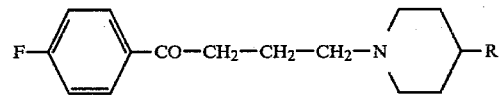

wherein R is lower alkyl having 1 to 6 carbon atoms, or pharmaceutically acceptable acid addition salts thereof.

A further advantage obtained with the method of this invention is that litters of piglets increase in weight compared to litters which are left untreated.

The preferred compound is 4-fluoro-γ-(4-methyl-piperidino)-butyrophenone which preferably is administered in an amount of 2 to 6 mg per kg body weight to pigs suffering from diarrhoea and in an amount of 0.1 to 2 mg per kg body weight to men suffering from travellers' diarrhoea.

The butyrophenone derivatives employed in the method of this invention can be administered orally or parenterally in combination with non-toxic liquid or solid carriers.

DETAILED DESCRIPTION OF THE INVENTION

The effect of melperone on diarrhoea associated with *E. coli* infections has been tested in laboratory investigations and clinical trials.

The laboratory tests were performed as described by Lönnroth et al., Infect. Immun. 1979, 24, 900–905. The results are shown in Table I. It is evident that melperone inhibits the intestinal fluid secretion indicating an effect on the adenylate cyclase system in intestinal mucosa. In case of melperone this inhibition is a more specific one compared to chlorpromazine and haloperidol (4'-fluoro-4-hydroxy-4-(4-chlorophenyl)-piperidinobutyrophenone), which drugs also block dopamine stimulated adenylate cyclase in brain tissue (Table I). In addition to this direct effect of melperone on the intestinal adenylate cyclase system, which is also seen after treatment with chlorpromazine, melperone shows pronounced antianxiety properties which may have some significant role in regulating intestinal electrolyte transport. This may be of importance as we know that stress conditions aggravate the outbreak of profuse diarrhoea.

The clinical trials were performed in a farm where outbreaks of profuse watery diarrhoea occurred among piglets. Three different double blind experiments were performed in piglets with an average weight of about 5 kg.

EXPERIMENT I

Every second litter suffering from diarrhoea was treated with 1.5 mg melperone intramuscular per kg body weight and every second litter with 25.0 mg Tylosin (The Merck Index, 9th Ed., 9486) intramuscular per kg body weight. In this experiment only the time of reversal of diarrhoea and the number of piglets who died were recorded. In each group 40 piglets were treated.

The results indicated that diarrhoea ceased more rapidly in the litters treated with melperone compared to Tylosin. Two piglets died in the group treated with Tylosin and none in the group treated with melperone.

EXPERIMENT II

Every second litter with profuse diarrhoea was treated with 1.5 mg melperone per kg body weight and every second litter with 6.7 mg trimetoprim (The Merck Index, 9th Ed., 9377)+25.0 mg sulfadoxin (The Merck Index, 9th Ed., 8697) (Borgal, Hoechst AG) per kg body weight. Before treatment each piglet within a litter was inspected, eartagged and the weight was recorded. As not all of the piglets in every litter suffered from diarrhoea, five groups of experimental piglets were obtained as follows:

(1) Piglets with diarrhoea treated with melperone.
(2) Piglets with diarrhoea treated with Borgal.
(3) Piglets without diarrhoea treated with melperone.
(4) Piglets without diarrhoea treated with Borgal.
(5) Piglets without diarrhoea and untreated.

Each pig participating in the experiments was inspected the day after treatment for presence of diarrhoea and the weight was recorded 7, 14 and 21 days after treatment. All piglets who died were necrospied. Fecal samples were obtained from every tenth piglet with diarrhoea for bacteriological examination.

EXPERIMENT III

Treatment with Borgal was compared to melperone (dosage 3.0 mg/kg body weight). The other experimental conditions were the same as in experiment II. The results are summarized in Tables IV and V.

The use of melperone compared to Borgal (trimetoprim-sulfadoxin) indicates that diarrhoea stopped in about the same percentage after one treatment. The mortality was low after both treatments and no significant differences between the two drugs were noticed. Melperone has certain advantages compared to antibiotics since no resistance can be awaited. In addition to this the side effects of chlorpromazine used as inhibitor of the adenylate cyclase system do not appear after the use of melperone.

EXPERIMENT IV

In a litter of twelve piglets suffering from diarrhoea which was left untreated, ten of the piglets died.

Piglets treated once and in which no diarrhoea was observed after one day are recorded as group A (Table II). Piglets treated twice one day apart are recorded as group B. Piglets treated three times one day apart are recorded as group C. Untreated piglets are recorded as group D and the untreated controls not suffering from diarrhoea are recorded as group E. The results are summarized in Tables II and III.

TABLE I

| Substance | Inhibition of cholera-induced diarrhoea $IC_{50}$ mg/kg | Inhibition of DA-stimulated cyclic AMP $IC_{50}$ $10^{-6}$M |
|---|---|---|
| Chlorpromazine | 1.5 | 0.41 |
| Haloperidol (4'-fluoro-4-hydroxy-4-(4-chlorophenyl)piperidino-butyrophenone | >>5.0 | 0.45 |
| Melperone | 2.9 | 7.10 |

Half-maximal inhibition ($IC_{50}$ mg/kg) estimated 4 hours after challenge with 10 μg of choleratoxin (to the intestine). The drug was given i.m. 1 hour before the choleratoxin. The drug concentrations causing 50% inhibition of DA-stimulated cyclic AMP ($IC_{50}$, $10^{-6}$M) in striatal homogenates by 80 uM dopamine (DA).

TABLE II

|  | Group | | | | Mortality | Daily weight gain (g) Group | | | |
|---|---|---|---|---|---|---|---|---|---|
|  | A | B | C | E |  | A | B | C | E |
| Borgal (diarrhoea) | 92 | 30 | 18 | — |  | 209 | 184 | 169 |  |
| Borgal (no diarrhoea) | 28 |  |  | — |  | 215 |  |  |  |
| Controls (no diarrhoea, untreated) |  |  |  | 35 |  |  |  |  | 210 |

No. of treated piglets in group A–C and the daily weight gain during three weeks after treatment (Exp. II).

TABLE III

|  | Group | | | | | Mortality | Daily weight gain (g) Group | | | |
|---|---|---|---|---|---|---|---|---|---|---|
|  | A | B | C | D | E |  | A | B | C | E |
| Melperone (diarrhoea) | 83 | 27 | 21 |  | — |  | 194 | 180 | 160 |  |
| Melperone (no diarrhoea) | 17 |  |  |  | — |  | 206 |  |  |  |
| Controls (no diarrhoea, untreated) |  |  |  |  | 15 | — |  |  |  | 205 |
| Controls (diarrhoea, untreated) |  |  |  | 12 |  | 10 |  |  |  |  |

No. of piglets in group A–E and the daily weight gain during three weeks after treatment. Dosage of melperone was 1.5 mg/kg body weight (Exp. II and IV).

TABLE IV

|  | Group | | | | Mortality | Daily weight gain (g) Group | | | |
| --- | --- | --- | --- | --- | --- | --- | --- | --- | --- |
|  | A | B | C | E |  | A | B | C | E |
| Borgal (diarrhoea) | 47 | 11 | 4 |  | 2 | 236 | 253 | 222 |  |
| Borgal (no diarrhoea) | 19 |  |  |  | — | 259 |  |  |  |
| Controls (no diarrhoea, untreated) |  |  |  | 20 |  |  |  |  | 253 |

No. of piglets in group A–E and the daily weight gain during three weeks after treatment (Exp. III).

TABLE V

|  | Group | | | | | Mortality | Daily weight gain (g) Group | | | |
| --- | --- | --- | --- | --- | --- | --- | --- | --- | --- | --- |
|  | A | B | C | D | E |  | A | B | C | E |
| Melperone (diarrhoea) | 48 | 12 | 10 |  |  | 4 | 227 | 206 | 233 |  |
| Melperone (no diarrhoea) | 10 |  |  |  |  | — | 247 |  |  |  |
| Controls (no diarrhoea, untreated) |  |  |  | 14 |  | — |  |  |  | 251 |
| Controls (diarrhoea, untreated) |  |  |  |  | 12 | 10 |  |  |  |  |

No. of piglets in group A–E and the daily weight gain during three weeks after treatment. Dosage of melperone was 3.0 mg/kg body weight (Ex. III and IV).

The compounds of the invention, together with conventional pharmaceutical carriers, can be employed in unit dosage forms such as solids, for example, tablets or capsules or liquid solutions, suspensions or elixirs for oral administration, and injections, or liquid solutions, emulsions and the like for parenteral use.

EXAMPLE 1

Sterile solution of injection

The following pharmaceutical compositions are formulated with the indicated amount of active agent using conventional techniques.

| Ingredients | Weight (mg) |
| --- | --- |
| Metylperone (4-fluoro-γ-(4-methyl-piperidino)-butyrophenone hydrochloride) | 20 |
| Sodium chloride | 9.3 |
| Sodium dihydrogen phosphate | 5.08 |
| Disodium edetate (ethylenediaminetetra-acetic acid disodium salt) | 0.2 |
| Benzyl alcohol | 40 |
| Sodium hydroxide | q.s. to adjust pH at 5.9–6.1 |
| Water double-distilled | q.s. to 2 ml |

Filtration through Membrane Filter, aseptic filling into ampoule and treatment in autoclave with streaming vapor for twenty minutes.

EXAMPLE 2

Tablets

Tablets suitable for oral administration which contain the following ingredients may be prepared by conventional techniques.

| Ingredients | Weight (mg) |
| --- | --- |
| 4-fluoro-γ-(4-methyl-piperidino)-butyrophenone hydrochloride | 5 |
| Magnesium stearate | 3 |
| Cellulose powder | 6 |
| Talcum | 3 |
| Lactose | 143 |
| Aerosil | 1 |

It is to be understand that the invention is not to be limited to the exact details of operation or exact compounds, compositions, methods, or procedures shown and described, as obvious modifications and equivalents will be apparent to one skilled in the art.

We claim:

1. A method of treating diarrhoea in mammals comprising administration to a mammal having diarrhoea of an effective amount of a compound selected from the group consisting of 4-fluoro-γ-(4-alkylpiperidino)-butyrophenone of the formula

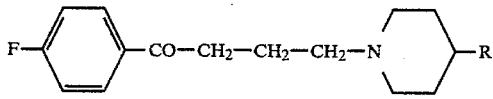

wherein R is lower alkyl having 1 to 6 carbon atoms, or pharmaceutically acceptable acid addition salts thereof.

2. The method of claim 1 wherein the active compound is administered in an amount of 0.1 to 20 mg per kg body weight to mammals.

3. The method of claim 1 wherein the compound is 4-fluoro-γ-(4-methyl-piperidino)-butyrophenone hydrochloride.

4. The method of claim 1 wherein about 2 to 6 mg per kg body weight of 4-fluoro-γ-(4-methyl-piperidino)-butyrophenone hydrochloride is administered to pigs.

5. The method of claim 1 wherein the compound is employed in admixture or conjunction with pharmaceutically acceptable carriers.

6. A method of treating traveler's diarrhoea in humans which comprises administering about 0.1 to 2 mg per kg body weight of 4-fluoro-γ-(4-methyl-piperidino)-butyrophenone hydrochloride to humans suffering from traveler's diarrhoea.

* * * * *